(12) United States Patent
Miyashita et al.

(10) Patent No.: US 6,867,002 B2
(45) Date of Patent: Mar. 15, 2005

(54) SAMPLE TREATING KIT AND SAMPLE TREATING METHOD USING THE SAME FOR ANALYSIS WITH A BIOSENSOR

(75) Inventors: Mariko Miyashita, Nishinomiya (JP); Toshihiko Yoshioka, Hirakata (JP); Shiro Nankai, Hirakata (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/420,719

(22) Filed: Oct. 20, 1999

(65) Prior Publication Data

US 2001/0049110 A1 Dec. 6, 2001

(30) Foreign Application Priority Data

Oct. 20, 1998 (JP) .......................................... 10-298896
May 25, 1999 (JP) .......................................... 11-145548

(51) Int. Cl.[7] ...................... G01N 33/53; G01N 33/543
(52) U.S. Cl. ........................ 435/7.1; 435/4; 435/174; 435/175; 435/176; 435/177; 435/183; 435/184; 435/188; 435/188.5; 435/262; 435/283.1; 435/286.1; 435/287.1; 435/287.2; 435/287.7; 436/43; 436/50; 436/55; 436/147; 436/174; 436/175; 436/176; 436/177; 436/178; 436/536; 436/543; 436/547; 436/825; 422/50; 422/105
(58) Field of Search .......................... 435/4, 7.1, 174, 435/177, 183, 184, 188, 188.5, 262, 283.1, 286.1, 287.1, 287.2, 287.7; 436/43, 50, 55, 147, 174–178, 536, 543, 547, 825; 422/50, 105

(56) References Cited

U.S. PATENT DOCUMENTS 3,856,469 A * 12/1974 Schneider et al. ......... 23/230 B
4,270,923 A * 6/1981 Kondo et al. ............. 23/230 B
4,431,507 A * 2/1984 Nankai et al. ............. 204/403
4,434,235 A * 2/1984 Rabi et al. .................. 436/110
4,654,311 A * 3/1987 Khanna et al. ............. 436/175
4,897,173 A * 1/1990 Nankai et al. ............. 204/403
5,079,170 A * 1/1992 Rosman et al. ............ 436/178
5,120,420 A * 6/1992 Nankai et al. ............. 204/403
5,124,253 A * 6/1992 Foulds et al. ................ 435/21
5,192,415 A * 3/1993 Yoshioka et al. .......... 204/403
5,229,282 A * 7/1993 Yoshioka et al. .......... 435/177
5,262,305 A * 11/1993 Heller et al. .................. 435/28
5,271,819 A * 12/1993 Bockowski ................ 204/402
5,272,054 A * 12/1993 Switchenko et al. .......... 435/4
5,326,449 A * 7/1994 Cunningham .............. 204/403
5,378,635 A * 1/1995 Yasuda et al. .............. 436/111
5,385,830 A * 1/1995 Amano et al. ................ 435/29
5,389,547 A * 2/1995 Tanaka et al. ................ 436/94
5,403,745 A * 4/1995 Ollington et al. ............. 435/11
5,492,834 A * 2/1996 Liu et al. ..................... 436/63
5,494,562 A * 2/1996 Maley et al. ............... 204/403

(List continued on next page.)

FOREIGN PATENT DOCUMENTS

| EP | 0 537 761 A2 | 4/1993 |
| EP | 0 732 406 A1 | 9/1996 |
| JP | 59006897 | 1/1984 |
| JP | 02240565 | 9/1990 |
| JP | 03090837 | 4/1991 |
| JP | 05240828 | 9/1993 |
| JP | 07083871 | 9/1993 |

*Primary Examiner*—Christopher L. Chin
*Assistant Examiner*—Kartic Padmanabhan
(74) *Attorney, Agent, or Firm*—Akin Gump Strauss Hauer & Feld, LLP (57) ABSTRACT

A sample solution treating instrument is provided for facilitating rapid and simplified adjustment of the condition of a sample solution proper for analysis with a biosensor before supplying the solution to the biosensor. The sample solution treating instrument includes, for example, a catalyst or an adsorbent which can remove any interfering substance in order to adjust the sample solution for measurement with a biosensor.

1 Claim, 4 Drawing Sheets

U.S. PATENT DOCUMENTS

| | | | | |
|---|---|---|---|---|
| 5,501,958 A | * | 3/1996 | Berry et al. | 435/18 |
| 5,571,419 A | * | 11/1996 | Obata et al. | 210/664 |
| 5,573,955 A | * | 11/1996 | Khanna et al. | 436/501 |
| 5,580,770 A | * | 12/1996 | DeFilippi | 435/180 |
| 5,582,697 A | * | 12/1996 | Ikeda et al. | 204/403.11 |
| 5,582,698 A | * | 12/1996 | Flaherty et al. | 204/409 |
| 5,628,897 A | * | 5/1997 | Phelan | 210/149 |
| 5,705,353 A | * | 1/1998 | Oh et al. | 435/7.92 |
| 5,755,953 A | * | 5/1998 | Henning et al. | 205/778 |
| 5,830,341 A | * | 11/1998 | Gilmartin | 205/777.5 |
| 5,932,174 A | * | 8/1999 | Brayton et al. | 422/79 |
| 5,935,442 A | * | 8/1999 | Lihme et al. | 210/656 |
| 5,945,345 A | * | 8/1999 | Blatt et al. | 436/518 |
| 5,985,116 A | * | 11/1999 | Ikeda et al. | 204/403 |
| 6,004,770 A | * | 12/1999 | Nelson | 435/23 |
| 6,007,775 A | * | 12/1999 | Yager | 422/57 |
| 6,183,740 B1 | * | 2/2001 | Short et al. | 424/94.6 |
| 6,379,883 B2 | * | 4/2002 | Davis et al. | 435/4 |

* cited by examiner

SAMPLE TREATING KIT AND SAMPLE TREATING METHOD USING THE SAME FOR ANALYSIS WITH A BIOSENSOR

BACKGROUND OF THE INVENTION

The present invention relates to an instrument for treating a sample solution to be supplied to a biosensor for analysis and a method for treating a sample solution using the same. More specifically, the present invention relates to a sample treating kit and a sample treating method using the same for analysis with a biosensor.

One method for simple quantitative measurement of a specific component contained in a sample solution is to determine oxidation current by reacting, in the presence of an electron acceptor, the specific component with an oxidoreductase corresponding to the substrate of the specific component and electrochemically oxidizing the reduced electron acceptor.

Biosensors using this measurement principle enable measurement of various substances if a proper oxidoreductase corresponding to the substrate of an analyte is selected.

However, since such biosensor makes analysis with the aid of enzyme reaction and electrode reaction, smooth progress of the enzyme reaction and electrode reaction is mandatory in order to improve measurement accuracy of the biosensor.

Therefore, there are several studies to enhance enzyme activity by adjusting temperature and pH of the sample solution or remove any interfering substance with the enzyme or electrode reaction.

Moreover, sample solutions may sometimes include oxidizable substances which may produce oxidation current due to their concurrent oxidation with the electron acceptor and generate a positive error in the measured oxidation current. This can result in impaired measurement accuracy of the biosensor. Therefore, reduction of adverse effects of such oxidizable substance to a minimum becomes a requisite.

Conventional biosensors are installed with means for solving the above-mentioned problems inside their measurement system.

Here, the operation of measurement of a flow injection analyzer (YSI MODEL 2700 SELECT, made by Yellow Spring Instrument Co., Inc.) as a biosensor using an immobilized enzyme membrane and electrode reaction will be described as one example.

The measurement system of this analyzer comprises an electrode system including at least a working electrode and a counter electrode, an immobilized enzyme membrane attached to the electrode system, a sample chamber to which a sample solution is supplied to make measurement there, and an electric circuitry connected to the electrode system.

First, one end of an aspiration tube for aspirating a sample whose other end communicates with the sample chamber is immersed in a sample solution and the solution is aspirated by the tube and supplied to the sample chamber through the communicating other end. At that time, a certain amount of buffer solution is aspirated by another aspiration tube and supplied to the sample chamber.

Subsequently, the sample solution and the buffer solution thus supplied are mixed by agitation using a stirrer installed in the sample chamber. When a certain time has passed after supply of the sample solution and buffer solution, electrochemical measurement is performed to quantitate the analyte in the sample solution.

Any analyzer having such structure adjusts pH of the sample solution to a suited pH for enzyme reaction and dilutes the sample solution to an appropriate concentration by supplying the buffer solution to the sample chamber.

Concurrent agitation of the sample solution and buffer solution facilitates their rapid mixing on one hand and promotes dissolution of the enzyme in the mixed solution on the other hand. This in turn enables supply of sufficient oxygen to proceed enzyme reaction.

Despite the above advantages, such analyzer requires exchange of the immobilized enzyme membrane with a proper one depending on the analyte. Moreover, since the pH range proper for enzyme reaction varies by enzyme, the buffer solution must be exchanged concurrently. This renders manipulation of the analyzer inconvenient.

Although dilution of the sample solution reduces adverse effects of the interfering substances hindering enzyme and electrode reactions and the oxidizable substance, complete elimination of these effects is much difficult. This limits the extent of improvement of the measurement accuracy.

BRIEF SUMMARY OF THE INVENTION

A primary object of the present invention is, therefore, to provide a sample solution treating instrument that facilitates simple adjustment of a sample solution to be supplied to a biosensor for analysis to a condition facilitating rapid analysis with high accuracy.

Another object of the present invention is to provide a method for treating a sample solution to be supplied to a biosensor for analysis, using the above sample solution treating instrument.

The present invention provides a sample solution treating instrument for formulating a sample solution to be supplied to a biosensor for analysis, comprising control means for placing the sample solution in a proper condition for analysis with the biosensor.

The method for treating a sample solution in accordance with the present invention comprises the steps of introducing a sample solution, which will be supplied to a biosensor for analysis, into the above sample solution treating instrument, and adjusting the sample solution closest to a proper condition for analysis with the biosensor.

In a preferred mode of the present invention, the control means has a catalyst located inside the instrument for converting an interfering substance in the sample solution to a harmless substance having no adverse effect on the measurement results.

In another preferred mode of the present invention, the control means has an adsorbent located inside the instrument for adsorbing and removing an interfering substance in the sample solution.

In a further preferred mode of the present invention, the control means has a buffer agent located inside the instrument for adjusting pH of the sample solution to a proper pH for the activity of an enzyme in the biosensor.

While the novel features of the invention are set forth particularly in the appended claims, the invention, both as to organization and content, will be better understood and appreciated, along with other objects and features thereof, from the following detailed description taken in conjunction with the drawings.

DETAILED DESCRIPTION OF THE INVENTION

As discussed above, the sample solution treating instrument in accordance with the present invention comprises control means which places a sample solution in a proper condition for analysis with a biosensor, namely, controls the condition of the sample solution by eliminating adverse influences of the above-mentioned interfering substances on the measurement results or controls the sample solution to have an adequate pH range or temperature range for the activity of an enzyme to be used. Pretreatment of the sample solution with this treating instrument facilitates rapid and high accuracy analysis of any specific component contained in the sample solution.

When the control means has a substance which catalyzes conversion of the above-mentioned interfering substance to a harmless substance having no effect on the measurement results, then it is possible to remove the effect of such interfering substance.

For example, when a sample solution containing an oxidizable interfering substance is used, if the treating instrument is provided with a catalyst layer containing an enzyme which catalyzes oxidation of this interfering substance or a metal oxide such as manganese dioxide, etc., the interfering substance is oxidized upon supply of the sample solution to the treating instrument and is converted to a harmless substance at no risk of producing oxidation current. This results in improved measurement accuracy of the biosensor.

Exemplary oxidizable substances include a variety of vitamin, such as vitamin $B_2$, vitamin C, etc., dyes such as anthocyanin, tannic acid, etc., and organic acids such as uric acid, etc. When the sample solution contains, for instance, ascorbic acid, namely vitamin C, inclusion of ascorbate oxidase in the catalyst layer may result in successful conversion of ascorbic acid to dehydroascorbic acid which is much refractory to oxidation.

Alternatively, the catalyst layer may contain a catalyst which converts such substance to which the enzyme contained in the biosensor mistakenly reacts by taking it as an analyte, into a substance to which the enzyme is least likely to react.

The catalyst layer may contain a single enzyme. However, inclusion of two or more enzymes in the catalyst layer proves particularly convenient when the sample solution contains two or more interfering substances, because this facilitates treatment of the sample solution by only one operation.

When the control means has an adsorbent having a physically adsorbing ability, it is possible to remove the interfering substance from the sample solution.

For example, organic acids such as lactic acid generating during brewing foods impair accuracy of the measurement of glucose concentration for quality control of brewed foods, because they have adverse effects on the enzyme reaction and electrode reaction.

The measurement accuracy, however, can be improved by treating the sample solution to remove such organic acids, using a treating instrument formed with an adsorbent layer containing activated carbon.

Alternatively, when the control means has a buffer agent which can be dissolved in the sample solution upon supply of the sample solution to the treating instrument and places the sample solution in a proper pH range for the activity of the enzyme used, the enzyme activity in the biosensor can be enhanced and rapid measurement can be performed with high accuracy.

For example, when lactate oxidase is the enzyme to be used, the use of a buffer agent such as phosphate buffer is better in order to place the sample solution in a pH range between 6 and 7 which is adequate pH range for the activity of lactate oxidase. Any arbitrary buffer agent, such as McIlvaine buffer or Tris-HCl buffer, may be used depending on the enzyme to be used.

Resins are suitable for constituting the treating instrument in accordance with the present invention. However, the present invention is not limited to the resin and any material that permits formation of the above-mentioned control means can be used.

As to the shape, the treating instrument in accordance with the present invention is not limited to a specific shape and any shape that can accommodate the above-mentioned control means and retain the sample solution may be used.

As to the location of the control means, it can be located at an arbitrary site which can make contact with the sample solution when the sample solution is supplied to the treating instrument.

A provision of heating means to the treating instrument enables direct supply of a sample solution shortly after being taken out from a low temperature reservoir, such as refrigerator, to a biosensor for measurement. Furthermore, not limited to enzyme, normal catalysts have a temperature at which they can exert their best activity. Therefore, controllability of the temperature of the sample solution at such temperature is considered much convenient, because this enables rapid completion of treatment and analysis of the sample solution.

As the heating means, it is recommended to cover the treating instrument with an electric heating sheet such as a textile incorporated with heating wires.

It is also recommended to include stirring means in the treating instrument, because it helps to mix the sample solution with the catalyst layer or a layer of buffer agent homogeneously.

The method for treating a sample solution in accordance with the present invention comprises the steps of introducing a sample solution to be supplied to a biosensor for analysis into the sample solution treating instrument as explained above, and adjusting the sample solution closest to a proper condition for the measurement with the biosensor.

This structure eliminates laborious manipulations, such as dilution of sample solution, for reducing adverse effects of any interfering substance contained in the sample solution after its introduction into a biosensor.

The biosensor has a tendency of losing its measurement accuracy with increases of analyte concentrations in the sample solution. Therefore, diluting the sample solution to an adequate magnification by supplying water, buffer solution and so on enhances measurement accuracy of the biosensor.

In doing so, it is recommended to use a buffer solution that can place the sample solution in a proper pH range for the activity of the enzyme in the biosensor.

Supplementary agitation and/or heating of the sample solution would accelerate the treatment of sample solution.

As the biosensor used here, disposable biosensors as described below are convenient. Although the sensors used in the following examples have no cover member, the use of commercially available sensors having a cover member for covering the base plate and forming, between the base plate and the cover member, a sample supply pathway for introducing a sample solution into the reaction layer is recommended. U.S. Pat. No. 5,120,420 which discloses details of such sensor with a cover member is incorporated herein by reference.

In the following, the present invention will be described more specifically by way of concrete examples.

Figure 1:
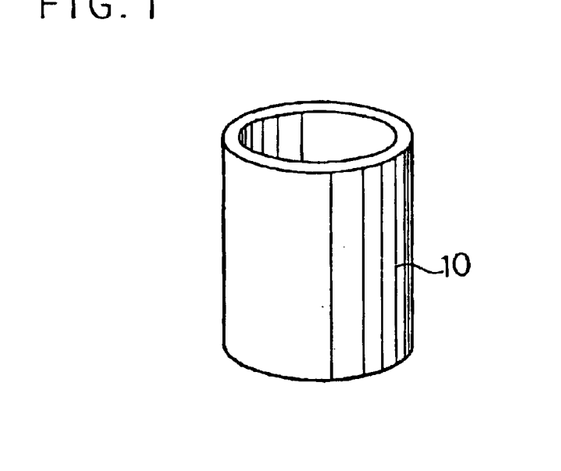
FIG. 1 is a perspective view illustrating an appearance of a sample solution treating instrument in accordance with one example of the present invention.
Figure 2:
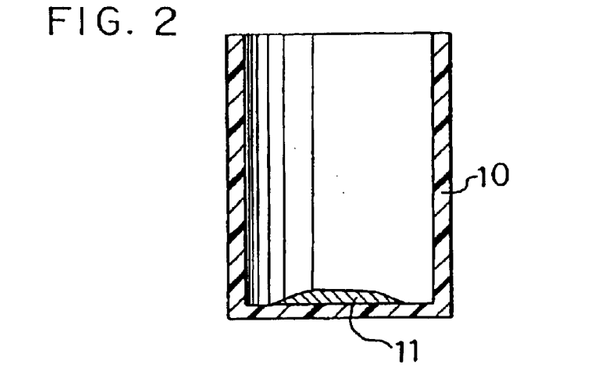
FIG. 2 is a longitudinal cross-sectional view of the treating instrument of FIG. 1.

FIG. 1 is a perspective view illustrating a sample solution treating instrument in accordance with one example of the present invention and FIG. 2 is a longitudinal cross-sectional view of FIG. 1.

A control membrane 11 is formed by either directly pressing a substance serving as means for placing a sample solution in a predetermined condition against a bottom of a resin vessel 10, or dropping a solution dissolving the substance in a proper solvent or a dispersion of the substance in a proper dispersion medium on the bottom, followed by drying and volatilizing the solvent or the dispersion medium.

Figure 3:
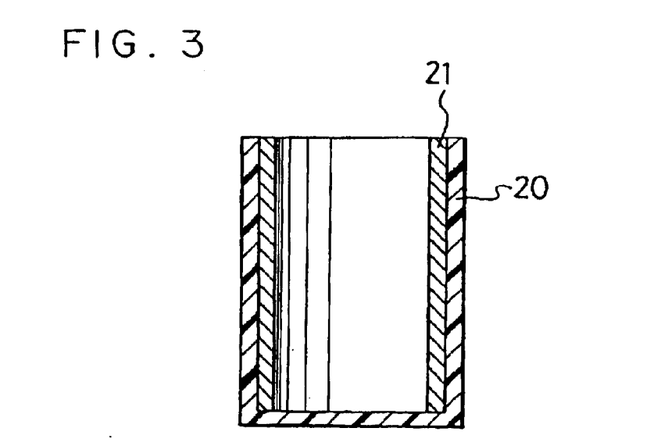
FIG. 3 is a longitudinal cross-sectional view illustrating a sample solution treating instrument in accordance with another example of the present invention.

FIG. 3 is a longitudinal cross-sectional view illustrating a sample solution treating instrument in accordance with another example of the present invention. A control membrane 21 is formed on an inner wall of a resin vessel 20 in the same manner as in FIG. 2.

Figure 4:
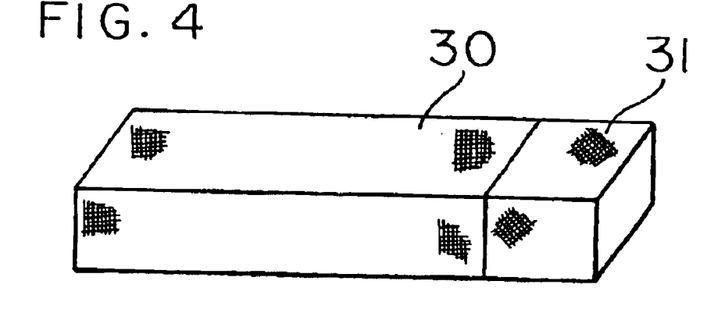
FIG. 4 is a perspective view illustrating a sample solution treating instrument in accordance with a further example of the present invention.

FIG. 4 is a perspective view illustrating a sample solution treating instrument in accordance with a further example of the present invention.

The treating instrument is composed of a sample treating unit 30 comprising a porous carrier, such as nonwoven glass fiber cloth or filter paper, and a sample supply unit 31. The sample treating unit 30 retains a substance for placing the sample solution in a desired condition. The sample treating unit 30 can be formed by dissolving the substance in an appropriate solvent in which the porous carrier is immersed and dried to volatilize the solvent or, alternatively, by dropping a solution dissolving the substance or a dispersion of the substance in a dispersion medium on the porous carrier and drying it to volatilize the solvent or dispersion medium. The sample supply unit 31 is made of an elastic material capable of retaining the sample solution insides, such as sponge. After passing through the sample treating unit 30, the sample solution reaches the sample supply unit 31 communicating with the sample treating unit 30 to be supplied to a biosensor therefrom.

Figure 5:
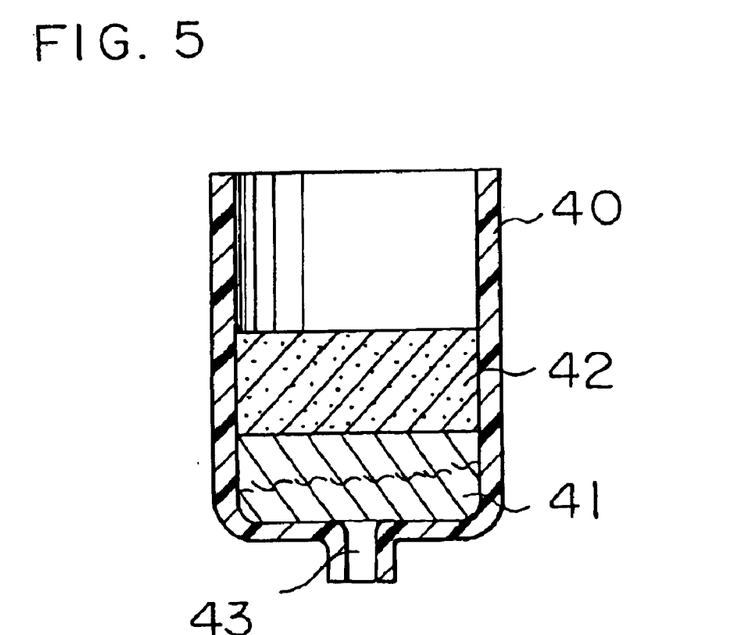
FIG. 5 is a longitudinal cross-sectional view of a sample solution treating instrument in accordance with a further example of the present invention.

FIG. 5 is a longitudinal cross-sectional view of a sample solution treating instrument in accordance with a further example of the present invention. Treating layers 41 and 42 are formed inside a resin vessel 40 equipped with a sample solution supply nozzle 43 on its bottom. The treating layers are made of the substance for placing the sample solution in a desired condition or a liquid permeable material retaining the substance. The sample solution to be treated is introduced into the vessel 40 through an opening of the vessel 40, treated during its passage through the treating layers 41 and 42, and supplied to a biosensor through the nozzle 43.

Figure 6:
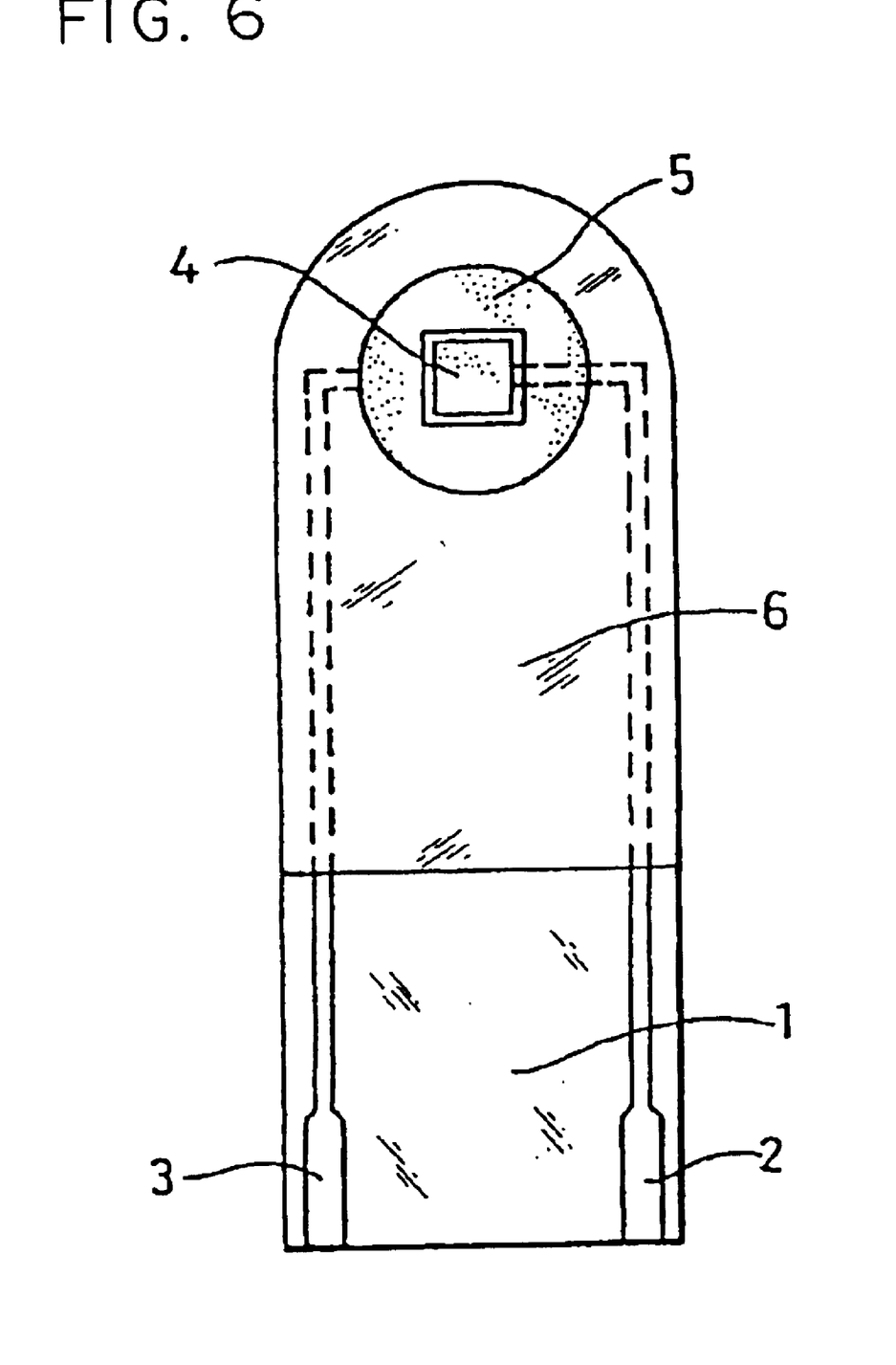
FIG. 6 is a plan view sketch illustrating a biosensor used in one example of the present invention from which a reaction layer has been omitted.

FIG. 6 is a plan view sketch illustrating a biosensor used in one example of the present invention from which a reaction layer has been omitted.

A silver paste is printed on an electrically insulating base plate 1 made of polyethylene terephthalate by known screen printing to form leads 2 and 3. Subsequently, a conductive carbon paste containing a resin binder is printed on the base plate 1 to form a working electrode 4. The working electrode 4 is so made to contact the lead 2. An insulating paste is further printed on the base plate 1 to form an insulating layer 6. The insulating layer 6 covers the periphery of the working electrode 4 to hold an exposed area of the working electrode 4 constant. Finally, the same conductive carbon paste containing a resin binder is printed on the base plate 1 to contact the lead 3 thereby forming a ring-like counter electrode 5.

Figure 7:
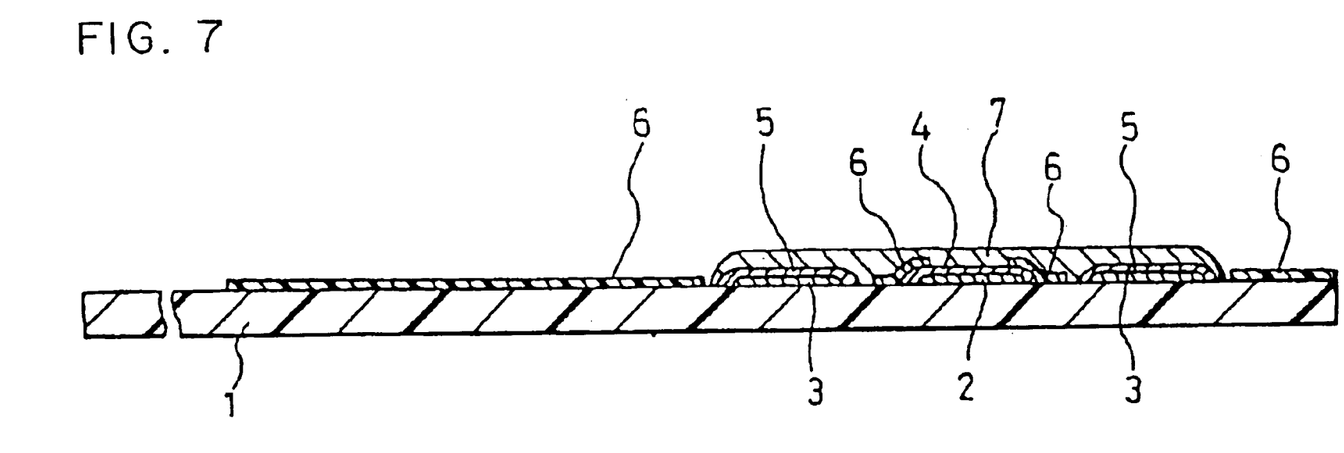
FIG. 7 is a longitudinal cross-sectional view illustrating the biosensor of FIG. 6.

FIG. 7 is a longitudinal cross-sectional view illustrating the biosensor of FIG. 6. A reaction layer 7 containing an enzyme and an electron acceptor is formed on the electrode system comprising the working electrode 4 and the counter electrode 5 on the base plate 1.

EXAMPLE 1

After preparation of a fruit juice as a sample solution, the glucose concentration in the fruit juice was measured using the biosensor illustrated in FIG. 6. The reaction layer 7 of the biosensor contained glucose oxidase (hereinafter abbreviated to "GOx") as the enzyme and potassium hexacyanoferrate (III) as the electron acceptor.

Fruit juices normally contain much ascorbic acid which is an oxidizable substance. Therefore, the use of fruit juices as they are can produce a positive error in the measured oxidation current and the obtained value will be higher than the actual value.

Therefore, prior to introduction into the biosensor, a fruit juice to be measured was adjusted using a treating instrument produced as follows.

An aqueous solution of ascorbate oxidase (hereinafter abbreviated to "AsOx") which is a catalyst of selective oxidation reaction of ascorbic acid was dropped on the bottom of the resin vessel 10 in FIG. 2 and dried in a dry atmosphere to form a layer 11 of AsOx, which gave a treating instrument to be used in this example.

A fruit juice was supplied to the treating instrument. As a result, the ascorbic acid contained in the fruit juice was converted to a harmless substance, dehydroascorbic acid, having no adverse influence on the measurement of oxidation current by the catalytic action of AsOx.

The fruit juice thus formulated was introduced into the biosensor as a sample solution. When dropped on the reaction layer 7 of the biosensor, the sample solution dissolved the reaction layer 7 and the GOx present in the reaction layer 7 selectively oxidized the glucose contained in the fruit juice. This enzyme reaction accompanied reduction reaction of the potassium hexacyanoferrate (III) to potassium hexacyanoferrate (II).

When a predetermined time has passed after the fruit juice was dropped, a voltage was applied, with reference to the counter electrode 5, onto the working electrode 4 to reoxidize the potassium hexacyanoferrate (II) to potassium hexacyanoferrate (III) and the oxidation current flowing during reoxidation reaction was measured.

The result showed successful measurement of the glucose concentration in the fruit juice with the same accuracy as the measurement of a glucose standard solution containing no ascorbic acid.

In measuring a fruit juice which was considered to contain much glucose, the fruit juice was diluted by concurrently supplying water to the treating instrument. The result showed that glucose quantitation was more accurate for the diluted sample solution than for the original sample solution.

When the fruit juice was adjusted to come in a proper pH range for the activity of AsOx using, as a diluent, a buffer solution with an adjusted pH between 4 and 8 in place of water, the measurement accuracy was further increased.

After being supplied to the treating instrument, the sample solution was stirred. This accelerated dissolution of the AsOx layer and facilitated supply of sufficient oxygen to the sample solution. Promoted catalytic reaction of the AsOx enabled rapid treatment of the sample solution.

Next, a fruit juice shortly after being taken out from a refrigerator was supplied to the treating instrument whose resin vessel as shown in FIG. 2 was covered with an electric heating sheet in order to warm up the fruit juice. As a result, since the fruit juice was successfully heated to a proper temperature for the activity of AsOx, the treatment was rapid. This fruit juice was supplied as it was to the biosensor for analysis in the same manner as described above which resulted in rapid and high accuracy analysis.

EXAMPLE 2

First, fruit fermentation mash generating in the course of fermentation of wine (hereinafter referred to as "must") was prepared as a sample solution and the glucose concentration in the must was measured using an identical biosensor to that of Example 1. Measurement and control of the glucose concentration in the must during fermentation is key to management of the quality of wine.

However, must normally contains much polyphenol such as tannic acid, for example, which is an oxidizable substance. Therefore, the use of such must as it is can produce a positive error in the measured oxidation current and the obtained value will be higher than the actual value.

Therefore, prior to introduction into the biosensor, a must to be measured was treated using a treating instrument produced as follows.

An aqueous solution of polyphenol oxidase (another name is laccase) which is a catalyst of selective oxidation reaction of polyphenol was dropped on the bottom of the resin vessel 10 in FIG. 2 and dried in a dry atmosphere to form an enzyme layer 11, which gave a treating instrument to be used in this example.

A must was supplied to the treating instrument. As a result, the polyphenol contained in the must was converted to a harmless substance, polyquinone, having no adverse influence on the measurement of oxidation current by the catalytic action of laccase.

The must thus formulated was introduced into the biosensor as a sample solution to measure the glucose concentration in the must in the same manner as in Example 1.

The result showed successful measurement of the glucose concentration in the must with the same accuracy as the measurement of a glucose standard solution containing no polyphenol.

In measuring a must which was considered to contain much glucose, dilution of the must by concurrently supplying water or a buffer solution at an adjusted pH between 4 and 8 similar to Example 1 enabled to increase the measurement accuracy.

EXAMPLE 3

A nutritional drink was prepared as a sample solution (RIPOVITAN D, manufactured by Taisho Pharmaceutical, Co., Ltd.) and fructose and glucose concentrations in the drink were measured in the same manner as in Example 1. At measurement of fructose concentration, fructose dehydrogenase was contained in the reaction layer 7 in place of GOx.

Luxury drinks like nutritional drink normally contain additives such as vitamin C (ascorbic acid) functioning as an antioxidant, vitamin $B_2$ (riboflavin) functioning as a dye. All of them are oxidizable substances and can produce a positive error in the measured oxidation current if used as they are, resulting in a higher value than the actual value.

Therefore, prior to introduction into the biosensor, a nutritional drink to be measured was treated using a treating instrument produced as follows.

An aqueous mixture of an aqueous AsOx solution and another aqueous solution of riboflavinase which is a catalyst of selective degradation of riboflavin at a volumetric ratio of 1:1 was dropped on the sample treating unit 30 in FIG. 4 and dried in a dry atmosphere to carry AsOx and riboflavin on the sample treating unit 30, which gave a treating instrument to be used in this example.

A nutritional drink was supplied to the sample treating unit 30 of the treating instrument. As a result, the vitamin C in the nutritional drink was converted, via the action of AsOx, to a harmless substance, dehydroascorbic acid, having no adverse influence on the measurement of oxidation current. Similarly, the vitamin $B_2$ was converted, via the action of riboflavinase, to a harmless substance, ribitol, having no adverse influence on the measurement of oxidation current.

The nutritional drink thus formulated during its passage through the sample treating unit 30 is introduced into the biosensor through the sample supply unit 31. Since the sample supply unit 31 is a sponge, the nutritional drink can be introduced into the biosensor by simply pressing the biosensor against the unit 31 and measurement can be initiated.

The nutritional drink thus formulated was introduced into the biosensor in the same manner as described above to measure the fructose and glucose concentrations in the drink.

The result showed successful measurement of the fructose and glucose concentrations in the drink with the same accuracy as the measurement of fructose and glucose standard solutions.

EXAMPLE 4

Glucose concentration was managed in the same manner as in Example 1 in the course of brewing Japanese rice wine (hereinafter referred to as "sake").

Fermentation of sake generates a variety of organic acids such as lactic acid, malic acid, etc., in addition to ethanol. Some of those organic acids may have adverse effects on the enzyme reaction and electrode reaction of the biosensor.

Therefore, prior to introduction into the biosensor, sake as a sample solution was treated using a treating instrument as described below.

The treating instrument used here has the structure as shown in FIG. 5. More specifically, it has a laminate of (1)

a treating layer 41 formed by pressing a mixture of an activated carbon powder with a powder of polytetrafluoroethylene at an appropriate ratio into a pellet and (2) a treating layer 42 formed by dropping a solution of a buffer agent on a glass filter and drying it to carry the buffer agent on the glass filter. The buffer solution is in a pH range between 4 and 7 at which GOx exhibits its best activity.

A sake moromi was supplied to the treating instrument in order to adjust its low pH between 3 and 4 to a proper pH at the treating layer 42 by means of the buffer agent and removing all organic acids contained in the moromi at the treating layer 41 by means of physical adsorption of activated carbon.

Measurement of the glucose concentration in the sample solution thus formulated in the same manner as in Example 1 was accurate.

In the foregoing example, although sake moromi was used as the sample to be treated with the treating instrument of the present invention, the instrument was similarly effective for removing ethanol and organic acids in the must of wine.

EXAMPLE 5

Using a medium under fermentation of lactic acid bacteria as a sample solution, the concentration of L-lactic acid in the medium was measured using the biosensor shown in FIG. 6. In this example, the enzyme was L-lactate oxidase (hereinafter abbreviated to "LOx") and the electron acceptor was potassium hexacyanoferrate (III).

Fermentation of lactic acid bacteria generates L-lactic acid with the progress of fermentation, which in turn changes the medium to acidic medium. The enzyme LOx in the biosensor decreases its activity rapidly when it has a pH value of 7 or less. Therefore, the use of a medium at advanced stages of fermentation for measurement with the biosensor can result in marked impairment of the measurement accuracy.

Therefore, the following treating instrument was produced for treating the medium as a sample solution in order to adjust pH of the sample solution.

The treating instrument was produced by spreading a dispersion of dipotassium hydrogenphosphate in toluene on the lateral wall of the vessel 10 in FIG. 3 and volatilizing toluene to form a control membrane 21.

The medium under fermentation of lactic acid bacteria was introduced into the treating instrument thus produced to adjust the pH of the medium to 7.

The medium thus formulated was introduced into the biosensor. A drop of the medium on the reaction layer 7 of the biosensor dissolved the reaction layer 7 and LOx in the reaction layer 7 selectively oxidized L-lactic acid in the medium. This enzyme reaction accompanied reduction reaction of the potassium hexacyanoferrate (III) to potassium hexacyanoferrate (II). Then, the reduced potassium hexacyanoferrate (II) was electrochemically reoxidized to potassium hexacyanoferrate (III) in the same manner as in Example 1 to measure oxidation current during the reoxidation reaction in order to determine the concentration of L-lactic acid in the medium. The result showed successful measurement with high accuracy.

As discussed above, the present invention enables rapid and simplified adjustment of the condition of a sample solution proper for analysis with a biosensor prior to its supply to the biosensor, thereby enhancing the measurement accuracy of the biosensor.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. A sample solution treating instrument comprising a sample treating unit and a sample supply unit, wherein the sample treating unit contains an agent that converts a sample solution to a condition for analysis with a biosensor that electrochemically measures a specific component in the sample solution, the agent selected from the group consisting of a catalyst that converts a first interfering substance in the sample solution to a harmless substance having no adverse effect on a measurement result of the specific component obtained by analysis with the biosensor, an adsorbent that adsorbs and removes a second interfering substance from the sample solution, and a buffer agent that adjusts a pH of the sample solution to a pH range adequate for an activity of an enzyme in the biosensor, and the sample supply unit is made of an elastic material that retains the sample solution inside the sample supply unit, wherein the sample supply unit is located adjacent to the sample treating unit such that the sample solution passes through the sample treating unit to the sample supply unit after treatment, but wherein the instrument is not physically coupled to a biosensor, wherein the first interfering substance and the second interfering substance may be the same or may be different.

* * * * *